United States Patent [19]

Bartholomey et al.

[11] Patent Number: 5,614,200
[45] Date of Patent: Mar. 25, 1997

[54] MASCARA COMPOSITIONS

[75] Inventors: Edward M. Bartholomey, Baltimore, Md.; John M. Gilley, Shrewsbury, Pa.; Magda El-Nokaly, Cincinnati, Ohio

[73] Assignee: The Procter & Gamble Company, Cincinnati, Ohio

[21] Appl. No.: 396,845

[22] Filed: Mar. 1, 1995

Related U.S. Application Data

[63] Continuation-in-part of Ser. No. 344,314, Nov. 22, 1994.
[51] Int. Cl.$^6$ .............................. A61K 7/02; A61K 7/032
[52] U.S. Cl. ................................ 424/401; 424/63; 424/64
[58] Field of Search ................................ 424/63, 64, 401

[56] References Cited

U.S. PATENT DOCUMENTS

| | | | |
|---|---|---|---|
| 4,871,536 | 10/1989 | Arraudeau et al. | 424/59 |
| 4,988,502 | 1/1991 | Ounanian et al. | 424/63 |
| 5,085,856 | 2/1992 | Dunphy et al. | 424/64 |

FOREIGN PATENT DOCUMENTS

| | | | |
|---|---|---|---|
| 0596465A1 | 5/1994 | European Pat. Off. | A61K 7/032 |
| 93/17659 | 9/1993 | WIPO | A61K 7/42 |

OTHER PUBLICATIONS

"Central Soya, Naturally", Customer Specification: Centrolex F, Jul. 1, 1980 Harry's Cosmeticology, 7th Ed., p. 684, 1982.

*Primary Examiner*—Thurman K. Page
*Assistant Examiner*—Sharon Howard
*Attorney, Agent, or Firm*—John M. Howell; David L. Suter; Jacobus C. Rasser

[57] ABSTRACT

The present invention is for mascara compositions having improved application characteristics. Said improvement is attributed to incorporation of a setting rate agent which delays the setting of the composition long enough to provide sufficient time to distribute the mascara in semi-liquid form onto the lashes as well as contribute to lash-thickening properties while avoiding negative aesthetics.

17 Claims, No Drawings

MASCARA COMPOSITIONS

This application is a continuation-in-part of U.S. patent application Ser. No. 08/344,314 filed Nov. 22, 1994.

TECHNICAL FIELD

The present invention covers oil-in-water mascara compositions having improved application characteristics. Said improvement is attributed to incorporation of a material in the presence of water which delays the setting of the film long enough to provide sufficient time to distribute the mascara in semi-liquid form onto the lashes which contributes to lash-thickening properties while avoiding negative aesthetics.

BACKGROUND OF THE INVENTION

Mascara compositions are pigmented compositions for application to eyelashes and eyebrows to beautify the eyes by providing desirable appearances such as thickening, lengthening, coloring, and defining the individual lashes.

Mascara is known to take a vast number of forms including cakes or blocks, creams, gels, and low viscosity liquids. Cake mascaras were originally the most popular form of this cosmetic. Their composition was made up of at least 50% soap whereby the pigment was mixed with the soap and stamped into cakes. With a wet brush, it could be lathered and then applied to the lashes resulting in a satisfactory, smooth application. Its primary drawback was that the film on the lashes was very water soluble and prone to smudging and running of the product transferring to the skin around the perimeter of the eye. Later on, improvements were made to the cake mascara which incorporated waxes to improve the water-resistance over the original soap-based form. This was usually at the expense of the smoothness of application.

With the advent of the automatic applicator, spiral-tipped wand or wand and brush applicator, cream and liquid mascaras came into being. Cream mascaras were usually dispersions of waxes and pigments in water with the end consistency very much like a vanishing cream. Combined with an automatic applicator, they soon surpassed the cake mascara in popularity due to their convenience of use which was less dependent upon actual technique by the user than the cake-based applicators. Most of the ingredients were similar to the improved form of the cake mascara and so many of the same shortcomings were still inherent. However, because it was a cream texture, the concentration of water was greater and allowed for the incorporation of natural and synthetic film-formers to help improve wear. The primary drawback of adding these film-formers was that the application time was shortened. As the water evaporated, the polymers coalesced and formed a film which resulted in increased clumping of the mascara on the lashes. Clumping upon application remained as a problem. To solve this dilemma various types of liquids were included into mascara formulations.

Incorporating liquid materials which are either non-volatile or evaporate more slowly than water, eases application of the mascara composition onto the lashes and reduces clumping. Such liquid materials includes humectants like propylene glycol, glycerine, and volatile components such as cyclomethicone and petroleum distillates, and natural or synthetic oils such as mineral oil or dimethicone. However, since these materials are liquids they do not effectively contribute substantially to the lash thickening properties of the mascara as would solid, semi-solid, or mesomorphic ingredients. Additionally, these materials can create problems in the formulation since they exist as liquids. In sufficient concentrations, they increase the solubility of the mascara film with respect to water, tears, sebum, and oils resulting in a potential for smudging. Similarly, they can also decrease the strength of the film or melting point of the wax phase resulting in a greater potential for smearing to occur.

Therefore, there is a need to have a mascara containing a material which when incorporated into a mascara composition controls the setting rate of the composition to provide sufficient time to distribute the mascara in semi-liquid form onto the lashes and contributing lash-thickening properties while avoiding negative aesthetics.

SUMMARY OF THE INVENTION

The present invention is for a mascara having improved application benefits to the eyelashes wherein said composition has improved application benefits, while avoiding the negatives associated with compositions currently known in the art. Said composition comprises:

a. from about 20% to about 65% solids;

b. from about 20% to about 80% liquid vehicle; and c. from about 8% to about 50% a setting rate agent;

wherein said setting rate agent enables said composition to maintain its liquid state after initial application to the lashes for a period sufficient to provide uniform distribution of said composition over the lashes. Such application benefits are responsible for improved appearance of the eyelashes.

Said setting rate agent comprises a mixture of glycerol monostearate and lecithin wherein the ratio of glycerol monostearate to lecithin is from about 2:1 to about 20:1.

A. Solids

In the present invention, solids are defined as materials which are solid or semi solid at their steady state and at ambient temperatures. Said solids include, but are not necessarily limited to waxes, fats, oils, pigments, dyes, gums, resins, inorganic and organic materials, fillers, thickeners, gelling agents, and mixtures thereof which are conventionally incorporated into eye makeup compositions. Solids comprise from about 20% to about 65%, preferably from about 30% to about 55%, and most preferably from about 40% to about 50% of the mascara composition of the present invention.

1. Waxes

Waxes comprise the highest levels of solids in the mascara composition of the present invention. Waxes are typically used at levels from about 5% to about 30%, preferably from about 10% to about 25% and most preferably from about 10% to about 20% by weight of the solids contained in the present invention.

Waxes are defined as lower-melting organic mixtures or compounds of high molecular weight, solid at room temperature and generally similar in composition to fats and oils except that they contain no glycerides. Some are hydrocarbons, others are esters of fatty acids and alcohols. Waxes useful in the present invention are selected from the group consisting of animal waxes, vegetable waxes, mineral waxes, synthetic waxes petroleum waxes, ethylenic polymers, hydrocarbon types such as Fischer-Tropsch waxes, silicone waxes, and mixtures thereof wherein the waxes have a melting point between 55° and 100° C. and a needle penetration, as measured according to the American standard ASTM D5, of 3 to 40 at 25° C. The principle of the measurement of the needle penetration according to the standards ASTM D5 consists in measuring the depth, expressed in tenths of a millimeter, to which a standard needle (weighing 2.5 g and placed in a needle holder weighing 47.5 g, i.e. a total of 50 g) penetrates when placed on the wax for 5 seconds.

The specific waxes useful in the present invention are selected from the group consisting of beeswax, lanolin wax, shellac wax (animal waxes); carnauba, candelilla, bayberry (vegetable waxes); ozokerite, ceresin, (mineral waxes); paraffin, microcrystalline waxes (petroleum waxes); polyethylene, (ethylenic polymers); polyethylene homopolymers (Fischer-Tropsch waxes); $C_{24-45}$ alkyl methicones (silicone waxes); and mixtures thereof. Most preferred are beeswax, lanolin wax, carnauba, candelilla, ozokerite, ceresin, paraffins, microcrystalline waxes, polyethylene, $C_{24-45}$ alkyl methicones, and mixtures thereof.

2. Fats

Fats are glyceryl esters of higher fatty acids such as stearic and palmitic. Such esters and their mixtures are solids at room temperature and exhibit crystalline structure. Glycerides are typically used at levels from about 5% to about 50%, preferably from about 10% to about 25% and most preferably from about 10% to about 20% by weight of the solids contained in the present invention.

The fats employed according to the invention are selected from the group consisting of fats derived from animals, vegetables, synthetically derived fats, and mixtures thereof wherein said fats have a melting point from about 55° C. to about 100° C. and a needle penetration, as measured according to the American standard ASTM D5, from about 3 to about 40 at 25° C. Preferably the fats selected for use used in the present invention are selected from the group consisting of glyceryl monostearate, glyceryl distearate, glyceryl tristearate, palmitate esters of glycerol, $C_{18-36}$ triglycerides, glyceryl tribehenate and mixtures thereof.

3. Pigments

The solids component of the mascara compositions of the present invention contains cosmetically acceptable pigments selected from the group consisting of inorganic pigments, organic pigments, and pearlescent pigments. When employed, the pigments are present in proportions depending on the color and the intensity of the color which it is intended to produce. The level of pigments in the solid portion of the mascara composition of present invention is from about 3% to about 20%, preferably from about 5% to about 15% and most preferably from about 5% to about 10%. Pigments are selected from the group consisting of inorganic pigments, organic lake pigments, pearlesent pigments, and mixtures thereof. Said pigments may optionally be surface-treated within the scope of the present invention but are not limited to treatments such as silicones, perfluorinated compounds, lecithin, and amino acids.

Inorganic pigments useful in the present invention include those selected from the group consisting of rutile or anatase titanium dioxide, coded in the Color Index under the reference CI 77,891; black, yellow, red and brown iron oxides, coded under references CI 77,499, 77,492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

The organic pigments and lakes useful in the present invention include those selected from the group consisting of D&C Red No. 19 (CI 45,170), D&C Red No. 9 (CI 15,585), D&C Red No. 21 (CI 45,380), D&C Orange No. 4 (CI 15,510), D&C Orange No. (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430) and the dye or lakes based on Cochineal Carmine (CI 75,570) and mixtures thereof.

The pearlescent pigments useful in the present invention include those selected from the group consisting of the white pearlescent pigments such as mica coated with titanium oxide, bismuth oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof.

B. Liquid Vehicle

The liquid vehicle is at a level from about 20% to about 80%, preferably 35% to about 65%, and most preferably 40% to about 55% by weight of the mascara composition of the present invention.

Said liquid vehicle comprises materials in which the solid particles are suspended in. The liquid vehicle helps to control the overall evaporation rate and, therefore, complements the setting rate agent in controlling dumping of the lashes. Therefore, the liquid vehicle needs to be balanced in relation to the setting rate agent. Additional amounts of setting rate agent are needed in formulations whereby there is a lesser concentration of liquid vehicle or a quicker evaporation rate occurs due to higher levels of ethyl alcohol or higher levels of film-formers such as soluble polymers or latexes.

The liquid vehicle of the present invention is selected from the group consisting of water, ethyl alcohol, dihydric alcohols such as propylene and butylene glycol, polyols such as glycerin, and mixtures thereof. Preferably the liquid vehicle is a mixture of water and ethyl alcohol, most preferably in a ratio of water to ethyl alcohol from about 60:1 to about 4:1.

C. Setting Rate Agent

The present invention comprises a setting rate agent at a level from about 8.0% to about 50.0%, preferably 8.0% to about 20.0%, and most preferably 8.0% to about 15.0% by weight of the mascara composition of the present invention. The setting rate agent of the present invention comprises materials which prevents negative aesthetics associated with rapid evaporation of the liquid vehicle during application of the mascara, as best exemplified by the tendency of lashes clumping mentioned above.

Said setting rate agent of the present invention comprises a mixture of glycerol monostearate and lecithin. It has been surprisingly found that when high levels of lecithin, especially those containing high levels of phophatidyl choline, are combined with glycerol monostearate in the presence of water, the application of the mascara is enhanced since the setting rate of the vehicle is controlled to provide a more liquid characteristic to the mascara throughout the application process. Lecithin is well known for use in cosmetics wherein lecithin behaves as a surface active ingredient having both an affinity for water and lipids. Lecithin is defined as a mixture of phosphatides or phospholipid compounds derived from natural sources such as soybeans. The three major phosphatides are phosphatidycholine, phosphatidylethanolamine, and phosphatidylinositol. Although lecithin is known for use in cosmetic compositions including mascaras, the level of lecithin is typically limited to a maximum of about 1%. It is believed that this limitation results from lecithin's limited water solubility; its propensity to hydrolyze at extremes of pH; and its ability to provide nutritional support for bacteria, particularly when the environment is made up of water and materials such as as carbohydrates, proteins, and phospholipids; see *Encyclopedia of Shampoo Ingredients,* Anthony L. L. Hunting, Copyright 1983, p. 274.; see *Harry's Cosmeticology,* 7th Edition 1982, page 684. Furthermore, since lecithins containing oil are liquid and thus easier to handle on the industrial scale, oil-free lecithin is typically not preferred. Lastly, lecithin is also very hygroscopic and therefore its use in mascaras is normally limited to below 1.00% similar to humectants to minimize smudging of the mascara film.

In the present invention lecithin is at a level of at least 1% by weight of the composition, and the ratio of glycerol monostearate to lecithin is from about 2:1 to about 20:1, preferably from about 3:1 to about 12:1, and most preferably about 3.5:1 to about 10.5:1. The lecithin preferred in the present invention is selected from the group consisting of oil-free lecithin, concentrated fractions of lecithin, hydrogenated lecithins, and mixtures thereof wherein said lecithin has a phospholipid content of not less than 75% and with less than 5% free oil present. Examples of these are Centrolex F from Central Soya and the Phospholipon Series (50G, 80, 90, 100, etc.) from Nattermann Phospholipid. The composition of an oil-free lecithin in the present continuation-in-part for the invention should contain about 23% phosphatidyl choline, 20% phosphatidyl ethanolamine, and about 14% phosphatidyl inositol. The remainder of the oil-free lecithin is composed of other phospholipids, lipids, carbohydrates, triglycerides, and moisture.

The composition of fractionated lecithins in the present invention are composed primarily of phosphatidyl choline either with a normal fatty acid distribution as occurs in lecithin or through a hydrogenation process whereby the fatty acids consist primarily of saturated types such as stearic and palmitic. Phopholipon 80 which is mentioned in the present invention is composed of 76% phosphatidyl choline, 3% lyso phosphatidyl choline, 8% phosphatidic acid, 4% phosphatidyl ethanolamine, and 9% other lipids. Phospholipon 50 or 50G which are also mentioned in the present invention are similar to Phospholipon 80 but are less concentrated in phosphatidyl choline which represents 50% of the mixture. Phosphatidyl ethanolamine is present at 30% along with other components. Other fractionated lecithins are but not limited to Phospholipon 100, Phospholipon 90H, Phospholipon 90/906, and other commercially available fractionated lecithins.

D. Optional Ingredients

In the present invention numerous optional ingredients may be added to provide additional benefits other than that attributed to the invention as defined above. For example, it is preferred that the mascara composition of the present invention contain a preservative system to inhibit microbiological growth and maintain the integrity of the product. In the present invention, the preservative system does not have a detrimental effect on the composition.

Any optional ingredients known to those skilled in the art may also be used in the invention. Examples of optional ingredients are cosmetic fillers including, but not limited to, mica, talc, nylon, polyethylene, silica, polymethacrylate, kaolin, teflon; cosmetic preservatives including, but not limited to, methylparaben, propylparaben, butylparaben, ethylparaben, potassium sorbate, trisodium EDTA, phenoxyethanol, ethyl alcohol, diazolidinyl urea, imidazolidinyl urea, quaternium-15; Film-forming agents can also be used. These include, but are not limited to natural and synthetic film-forming agents such as shellac, PVP, PVP/VA Copolymer, acacia, hydroxyethylcellulose, PVP/DMEA, acrylic or silicone latexes, and polyquaternium-10.

Emulsifiers may also be used in the present invention in order to assist in the stabilization of the compositions. Said emulsifiers include, but, are not necessarily limited to the group consisting of soaps, phosphate esters, ethoxylated alcohols, ethoxylated fatty acids, ethoxylated fatty esters, polyol ether esters, glycerol esters, sucrose or sorbitan esters, glucose esters, potassium or DEA-cetyl phosphate, fatty esters and mixtures thereof.

PROCESS FOR MAKING MASCARA COMPOSITIONS

A black shade of mascara that is an oil-in-water emulsion can be prepared by blending together the ingredients of Examples I, II, and III as follows:

Place the waxes and fats into a vessel equipped with heating and mixing. Heat this lipid mixture to about 85° C. with low speed mixing until liquefied and homogeneous. With continued mixing add the pigments. Increase the mixing rate to high and mix until the pigments are uniformly dispersed throughout the lipid mixture; about 30–35 minutes. Add emulsifiers to said lipid mixture while continuing to mix. In a second vessel equipped with mixing and heating, add water and a polyme. If shellac is used, neutralize the polymer to a pH of 6.9–7.0 with triethanolamine. Mix with heat until this aqueous mixture is about 65° C. Add a sequestrant to said aqueous mixture and continue mixing and heating until the temperature of said aqueous mixture is about 85° C. Q.S. for any water loss from said aqueous mixture and slowly combine it with said lipid mixture. Mix without heating this combined mixture until the temperature of said combined mixture is from about 65° C.–70° C. Q.S. said combined mixture for any water lo loss, add the preservatives and mix until homogeneous. Cool said combined mixture to about 45° C.–47° C., wherein any remaining preservatives and optional components are added. Continue cooling and mixing until said combined mixture is about 27° C.–30° C. Transfer said combined mixture to suitable storage containers for subsequent filling in retail size packaging.

EXAMPLES

| FORMULATION 1 | |
|---|---|
| INGREDIENT | % W/W |
| Carnauba Wax | 3.50 |
| Glyceryl Monostearate[1] | 13.00 |
| White Beeswax | 3.25 |
| C18–C36 Triglycerides[2] | — |
| Hydrogenated Glycerol Rosinate[3] | 0.15 |
| Propylparaben | 0.15 |
| Paraffin Wax 118/125 | — |
| Paraffin Wax | — |
| Phospholipon 80[4] | 1.25 |
| Stearic Acid 3X | 2.75 |
| Oleic Acid | 0.75 |
| Triethanolamine | 1.75 |
| Propylene Glycol | 2.00 |
| Deionized Water | 43.32 |
| Shellac, NF | 3.00 |
| Ammonium Hydroxide (28%) | 0.30 |
| Trisodium EDTA | 0.10 |

-continued

FORMULATION 1

| INGREDIENT | % W/W |
| --- | --- |
| Black Iron Oxide | 7.25 |
| Simethicone | 0.20 |
| Methylparaben | 0.25 |
| Ethylparaben | 0.20 |
| Phenoxyethanol | 0.25 |
| Ethyl Alcohol 40B, 190 proof | 1.00 |
| Diazolidinyl Urea | 0.30 |
| Syntran 5170 | 15.00 |
| dl-Panthenol | 0.28 |
| Total | 100.00 |

[1]Available as Emerest 2400 from Henkel/Emery
[2]Available as Syncrowax HGL-C from Croda, Inc.
[3]Available as Foral 105 from Hercules, Inc.
[4]Available as Phospholipon 80 from American Lecithin.

FORMULATION 2

| INGREDIENT | % W/W |
| --- | --- |
| Carnauba Wax | 3.50 |
| Glyceryl Monostearate[1] | 9.00 |
| White Beeswax | 7.25 |
| C18–C36 Triglycerides[2] | — |
| Hydrogenated Glycerol Rosinate[3] | 0.1 |
| Propylparaben | 0.15 |
| Paraffin Wax 118/125 | — |
| Phospholipon 50G[4] | 0.75 |
| Phospholipon 80[5] | 0.50 |
| Stearic Acid 3X | 3.90 |
| Oleic Acid | — |
| Triethanolamine | 1.95 |
| Propylene Glycol | 2.00 |
| Deionized Water | 42.32 |
| Shellac, NF | 3.00 |
| Ammonium Hydroxide (28%) | 0.30 |
| Syntran 5170 | 15.00 |
| Black Iron Oxide | 7.25 |
| Simethicone | 0.20 |
| Methylparaben | 0.25 |
| Ethylparaben | 0.20 |
| Phenoxyethanol | 0.75 |
| Ethyl Alcohol 40B, 190 proof | 1.00 |
| Diazolidinyl Urea | 0.20 |
| Trisodium EDTA | 0.10 |
| dl-Panthenol | 0.28 |
| Total | 100.00 |

[1]Available as Emerest 2400 from Henkel/Emery
[2]Available as Syncrowax HGL-C from Croda, Inc.
[3]Available as Foral 105 from Hercules, Inc.
[4] & [5]Available as Phospholipon 80 & 50G from American Lecithin

What is claimed:

1. A mascara composition comprising:
   a. from about 20% to about 65% solids;
   b. from about 20% to about 80% liquid vehicle; and
   c. from about 8% to about 50% a setting rate agent comprising a mixture of glycerol monostearate and lecithin wherein lecithin is at a level of at least 1% by weight of the composition, and the ratio of glycerol monostearate to lecithin is from about 2:1 to about 20:1;
   wherein said setting rate agent enables said mascara composition to maintain its liquid state after initial application to the lashes for a period sufficient to provide uniform distribution of said mascara composition over said lashes.

2. A mascara composition according to claim 1 wherein said setting rate agent comprises a mixture of glycerol monostearate and lecithin wherein lecithin is at a level of at least 1% by weight of the composition, and the ratio of glycerol monostearate to lecithin is from about 3:1 to about 12:1.

3. A mascara composition according to claim 1 wherein said setting rate agent comprises a mixture of glycerol monostearate and lecithin wherein lecithin is at a level of at least 1% by weight of the composition, and the ratio of glycerol monostearate to lecithin is and most preferably about 3.5:1 to about 10.5:1.

4. A mascara composition according to claim 1 wherein said lecithin is selected from the group consisting of oil-free lecithin, fractionated lecithin, and mixtures thereof wherein said lecithin has a phospholipid content of not less than 75% and with less than 5% free oil present.

5. A mascara composition according to claim 1 wherein the solid portion comprises:
   (a) from about 5 to about 30% wax;
   (b) from about 5 to about 50% fats; and
   (c) from about 3 to about 20% pigments.

6. A mascara composition according to claim 1 wherein the liquid vehicle is selected from the group consisting of water, ethyl alcohol, dihydric alcohols, polyols and mixtures thereof.

7. A mascara composition according to claim 6 wherein the liquid vehicle is a mixture of water and ethyl alcohol.

8. A mascara composition according to claim 7 wherein the ratio of water to ethyl alcohol is from about 60:1 to about 4:1.

9. A mascara composition according to claim 5 wherein said wax is selected from the group consisting of animal waxes, vegetable waxes, mineral waxes, various fractions of natural waxes, synthetic waxes, petroleum waxes, ethylenic polymers, Fischer-Tropsch waxes, silicone waxes, and mixtures thereof wherein said wax has a melting point from about 55° C. to about 100° C. and a needle penetration, as measured according to the American standard ASTM D5, of 3 to 40 at 25° C.

10. A mascara composition according to claim 9 wherein said wax is selected from the group consisting of beeswax, lanolin wax, carnauba, candelilla, ozokerite, ceresin, paraffins, microcrystalline waxes, polyethylene, $C_{24-45}$ alkyl methicones, and mixtures thereof.

11. A mascara composition according to claim 5 wherein said fat is selected from the group consisting of fats derived from animals, vegetables, synthetically derived fats, and mixtures thereof wherein said fats have a melting point from about 55° C. to about 100° C. and a needle penetration, as measured according to the American standard ASTM D5, from about 3 to about 40 at 25° C.

12. A mascara composition according to claim 11 wherein the fats are selected from the group consisting of glyceryl monostearate, glyceryl distearate, glyceryl tristearate, palmitate esters of glycerol, $C_{18-36}$ triglycerides, glyceryl tribehenate, and mixtures thereof.

13. A mascara composition according to claim 5 wherein the pigment is selected from the group consisting of inorganic pigments, organic lake pigments, pearlesent pigments, and mixtures thereof.

14. A mascara composition according to claim 13 wherein said pigments are surface-treated.

15. A mascara composition according to claim 14 wherein said pigments are inorganic pigments selected from the group consisting of rutile and anatase titanium dioxide, black, yellow, red and brown iron oxides, manganese violet, ultramarine blue, chromium oxide, chromium hydrate, ferric blue and mixtures thereof.

16. A mascara composition according to claim 5 further comprising an emulsifier selected from the group consisting of soaps, phosphate esters, ethoxylated alcohols, ethoxylated fatty acids, ethoxylated fatty esters, polyol ether esters, glycerol esters, sucrose or sorbitan esters, glucose esters, potassium or DEA-cetyl phosphate, fatty esters and mixtures thereof.

17. A mascara composition according to claim 5 further comprising cosmetic fillers, preservatives, film-forming agents and mixtures thereof.

* * * * *